United States Patent

Weyl

[11] Patent Number: 5,949,023
[45] Date of Patent: Sep. 7, 1999

[54] TEMPERATURE-RESISTANT CABLE BUSHING AND METHOD FOR THE MANUFACTURE OF THE SAME

[75] Inventor: Helmut Weyl, Schwieberdingen, Germany

[73] Assignee: Robert Bosch GmbH, Stuttgart, Germany

[21] Appl. No.: 08/860,900

[22] PCT Filed: Oct. 24, 1996

[86] PCT No.: PCT/DE96/02051

§ 371 Date: Jul. 15, 1997

§ 102(e) Date: Jul. 15, 1997

[87] PCT Pub. No.: WO97/18610

PCT Pub. Date: May 22, 1997

[30] Foreign Application Priority Data

Nov. 15, 1995 [DE] Germany .......................... 195 42 650

[51] Int. Cl.⁶ .................................................. H01R 4/22
[52] U.S. Cl. ..................... 174/77 R; 174/85; 174/65 G
[58] Field of Search ............................. 174/74 A, 77 R, 174/93, 85, 65 G, 152 G, 153 G; 248/56

[56] References Cited

U.S. PATENT DOCUMENTS

| | | | |
|---|---|---|---|
| 4,019,974 | 4/1977 | Weyl et al. | 204/195 S |
| 4,627,647 | 12/1986 | Hauff | 174/65 G X |
| 4,675,937 | 6/1987 | Mitomi | 248/56 X |
| 5,213,290 | 5/1993 | Moretti | 248/56 |
| 5,540,450 | 7/1996 | Hayashi et al. | 174/65 G |
| 5,625,167 | 4/1997 | Von Noten et al. | 174/77 R |

FOREIGN PATENT DOCUMENTS 4126378 4/1992 Germany .
675179 8/1990 Switzerland .

*Primary Examiner*—Kristine Kincaid
*Assistant Examiner*—Chau N. Nguyen
*Attorney, Agent, or Firm*—Venable; Norman N. Kunitz; Ashley J. Wells

[57] ABSTRACT

A cable bushing in a housing for a device which may be a gas sensor and which may be connected to at least one connecting cable having an electrical conductor and cable insulation includes a molded body provided inside an opening of the housing and through which the at least one connecting cable is guided. The molded body has defined therein at least one bushing tube and has an outer cylindrical wall in which is defined a ring groove starting at one frontal side and extending axially inside the molded body, the at least one bushing tube and the ring groove being separated by an inner wall. The inner wall and the outer cylindrical wall of the molded body have respective thicknesses, and the thickness of the outer cylindrical wall is less than the smallest wall thickness of the inner wall. A support ring is positioned in the ring groove and serves as an outer support for wedging in the molded body into the opening of the housing. A method for producing the cable bushing includes inserting the at least one connection cable into the molded body while outside of the housing; subjecting the molded body and the inserted at least one connection cable to a heat treatment while outside of the housing so that the cable insulation can at least one of melt on and melt together with the molded body; inserting a support ring into the ring groove of the molded body; installing the molded body with the inserted at least one connection cable and support ring into an installed position within the housing; and pressing the molded body while in the installed position into the housing so that the molded body is wedged gas-tight into the housing.

2 Claims, 2 Drawing Sheets

TEMPERATURE-RESISTANT CABLE BUSHING AND METHOD FOR THE MANUFACTURE OF THE SAME

BACKGROUND OF THE INVENTION

1. Field of the Invention

The invention concerns a temperature-resistant, tightly sealed cable bushing in a housing, in particular in a gas sensor housing, with a molded body arranged inside the housing, through which at least one connecting cable with an electrical conductor and a cable insulation are fed, as well as a method for the manufacture of said cable bushing.

2. Description of the Related Art

Tightly sealed and high-temperature resistant cable bushings are required, for example, for gas sensors, in particular for Lambda probes. These gas sensors have a housing with a sensor element arranged on the inside. The sensor element is contacted inside the housing with connecting cables. The connecting cables exit the housing through a cable bushing. The gas sensors for determining the exhaust-gas composition in motor vehicles are inserted into the exhaust pipe and are thus subjected to the environmental influences prevalent there. The sensor element arranged inside the housing operates as a rule with reference air, which is fed into the housing, for example, via the cable insulation. However, it is critical on the other hand that the sensor element inside the housing does not come in contact with negative environmental influences such as dirt, oil and/or water. This necessitates that the cable bushing is designed such that it forms a tight seal against the housing as well as against the cable insulation.

From the Federal Republic of Germany Application No. 41 26 378 A1, a cable bushing is known for which the connecting cables are fed through an elastic, plug-like molded body. The molded body is composed of a temperature-resistant material, e.g. PTFE (TEFLON), and is enclosed and pressed together by a housing sleeve that forms the housing. An O-ring is additionally inserted as a seal between housing sleeve and molded body. The O-ring is composed of an elastomer, for example Viton, and has only a limited temperature stress tolerance. The use of this cable bushing at higher temperatures, such as are present if the gas sensor is arranged close to the motor exhaust, is therefore limited with respect to the temperature resistance of the seal.

SUMMARY OF THE INVENTION

In contrast, the invention provides a molded body designed with a ring groove, which starts on one frontal side and extends axially inside the molded body and forms a cylinder wall toward the housing, and a support ring is arranged inside the ring groove, and has the advantage that the cable bushing ensures a temperature-resistant, lasting and reliable seal. The design of the cylinder wall achieves that the material for the molded body does not flow too strongly when heated up, but retains its position between the supporting ring and the housing.

Owing to the measures listed in the dependent claims, advantageous embodiments and modifications of the invention are possible. In order to limit the flowability of the material for the molded body at higher temperatures, it is advantageous to keep the wall thickness for the molded body to a minimum between ring groove and housing sleeve. An especially suitable, tight connection between molded body and cable insulation can be achieved if both parts are composed at least partially of the same material. Particularly suitable as a material is PTFE (TEFLON), which has the advantage of having a high temperature resistance with simultaneously high sealing capacity.

BRIEF DESCRIPTION OF THE DRAWINGS

One exemplary embodiment of the invention is shown in the drawing and is explained in more detail in the description below.

DESCRIPTION OF THE PREFERRED EMBODIMENTS

Figure 1:
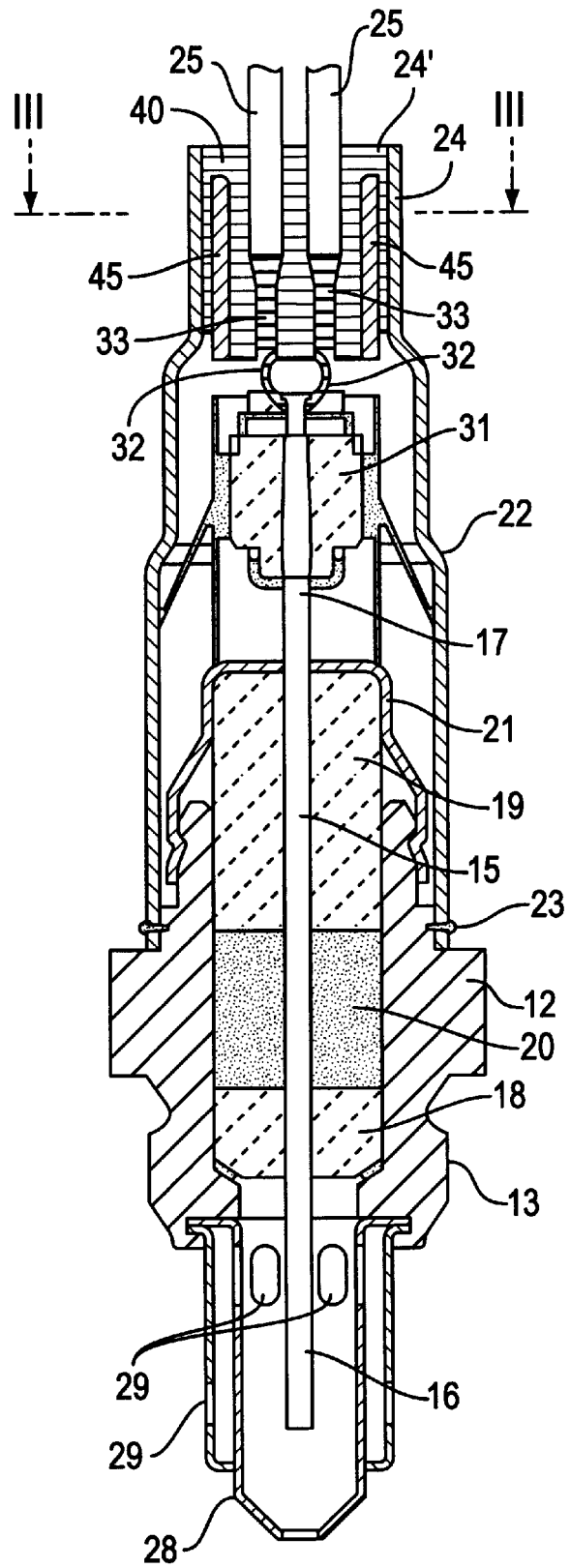
FIG. 1 shows a sectional view of a gas sensor.

FIG. 1 shows a gas sensor 10, for example an electrochemical oxygen sensor with a metal housing 12, having a thread 13 as fastening means for installation into a non-depicted measuring gas tube. A sensor element 15 with an end segment 16 on the measuring gas side and an end segment 17 on the connection side is arranged inside of housing 12. The sensor element 15 is held inside housing 12 by means of a first ceramic molded body 18 and a second ceramic molded body 19 and a sensor element seal 20 that is arranged between the two ceramic molded bodies 18, 19. The first ceramic molded body 18 rests axially on one shoulder of the housing 12. A pressure sleeve 21 acts upon the second ceramic molded body 19, which pressure sleeve engages in catches arranged on the housing 12. Pressure is exerted onto the sensor element seal 20 by means of the pressure sleeve 21, so that the presintered sealing powder fits itself against the wall of housing 12 and the sensor element 15, thereby producing a sufficient sealing effect.

A protective tube 28 with intake/outlet openings 29 for the measuring gas is fastened to the measuring gas side end of housing 12. The measuring gas side end segment 16 of the sensor element 15 projects into the protective tube 28.

The connecting-side end segment 17 of sensor element 15 has sensor element contacts for electrodes that are not shown and, if necessary, a heater. These contacts are contacted, for example with a two-part plug 31. The plug 31 has contacting parts 32, corresponding to the number of sensor element contacts, with respectively one crimp contact 33. The crimp contacts 33 are connected with connecting cables 25 to respectively one electrical conductor 26 and one cable insulation 27. PTFE (TEFLON) is used, for example, as material for the cable insulation 27.

The plug 31 is furthermore surrounded by a metal housing sleeve 22, which is welded gas-tight to the housing 12 at welding seam 22. At the end located opposite the housing 12, the housing sleeve 22 has a tapered section 24, for example, with a circular opening 24'. Inside the opening 24' of the housing sleeve 22 is a molded body 40, composed of a temperature-resistant material, e.g. of PTFE (TEFLON).

The mechanical qualities of the molded body 40 can be improved by using glass-fiber filled TEFLON, wherein it is also conceivable to have an inhomogeneous glass fiber filling, if necessary, so that pure PTFE is present in the border region between cable insulation casing and molded body.

Figure 2:
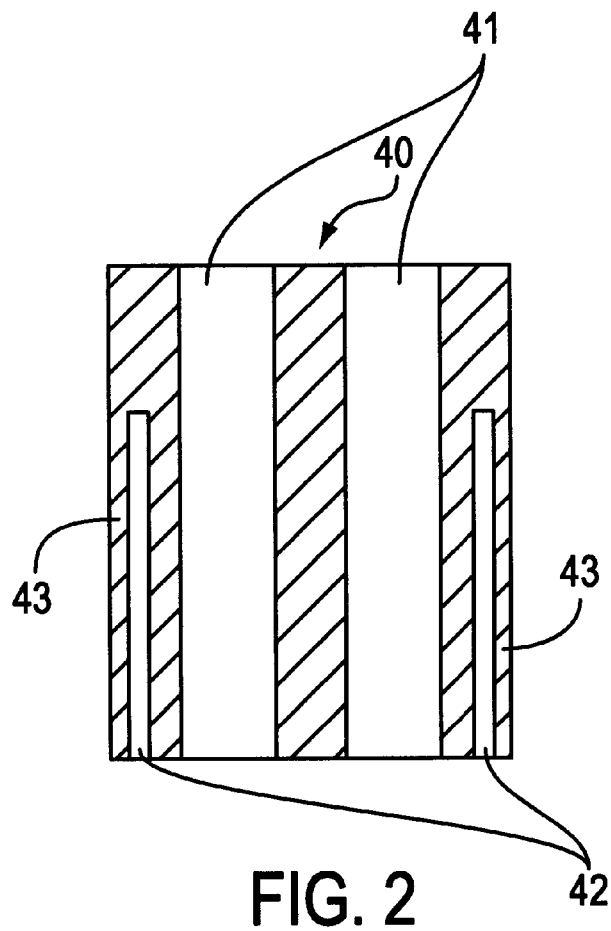
FIG. 2 shows a sectional view of a molded body for an inventive cable bushing.
Figure 3:
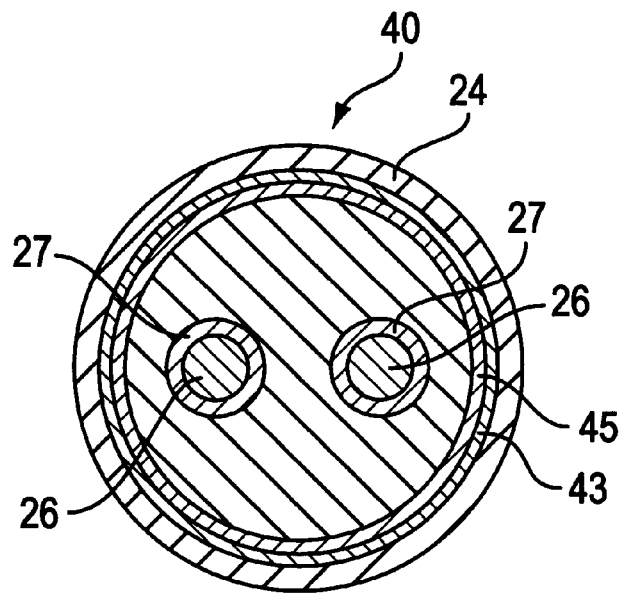
FIG. 3 shows a sectional view through the cable bushing for the gas sensor, along the lines III—III in FIG. 1.

According to FIGS. 2 and 3, for example, the molded body 40 has two cylindrical bushing tubes 41 for feeding through the connecting cables 25. If the sensor elements 15 are heated, then heater contacts are provided in addition to the electrode contacts. As a result of this, four connecting cables must be fed through to the sensor element 15. Of course, it is necessary to have four cylindrical bushing tubes 41 in that case. However, it is also conceivable to have applications with more than four connecting cables.

The molded body 40 furthermore has an axially extending annular ring groove 42 on the front pointing into the housing sleeve 22, so that an outer cylinder wall 43 forms in the region of molded body 40, which faces the housing sleeve 22. The at least one bushing tube 41 and the ring groove 42 are separated by an inner wall as shown in FIG. 2. As a practical matter, the wall thickness of the cylinder wall 43 is less than the thinnest wall thickness formed between ring groove 42 and bushing tube 41. However, it is also conceivable that the ring groove 42 is inserted from the opposite side into the molded body 40, so that the ring groove 42 points outward. The ring groove 42 can be produced, for example, with a core-hole drill. The wall thickness of cylinder wall 43 is selected as thin as possible, e.g., 0.2 to 1 mm, preferably 0.5 mm. A tube-shaped metal support ring 45 is positioned inside ring groove 42, in accordance with FIGS. 1 and 3.

In order to produce the cable bushing, the connecting cables 25 are initially fed through the cylindrical bushings 41 and are connected to the crimp contacts 33 of the respective contact parts 32. The crimp contacts 33 are pushed back into the bushings 41, so that the crimp contacts 33 are integrated into the molded body. As a result of this, the molded body 40 simultaneously functions as pull relief for the connecting cable 25. Subsequently, the molded body 40 with the inserted connecting cables 25 is clamped by a production tool that is not shown in more detail, wherein the production tool can be designed in the shape of a sleeve or in the shape of two clamping jaws. The molded body 40 is then heated, for example, in an oven, which causes the molded body 40 and the cable insulation 27 to expand. During this process, the possibly existing annular gaps around the insulation 27 for the cables are closed. In the course of heating up to 370° C., for example, pressure is exerted by the production tool onto the molded body 40. The TEFLON material becomes doughy during the heating of molded body 40 and can be deformed accordingly as a result of the pressure acting upon it, so that the border surfaces between cable insulation 27 and molded body 40 enclose each other in a form-fitting way, thereby causing a melting on or a melting together. This results in the desired tight connection between molded body 40 and cable insulation 27.

In the following step, the support ring 45 is inserted into the ring groove 42. However, the melting on or melting together of the molded body 40 and the cable insulation 27 can also occur while the support ring 45 is already inserted. After the molded body 40 is positioned in the opening 24' of the housing sleeve 22, a tool that is not shown is used to act from the outside upon the end segment 24 of the housing sleeve 22 in such a way that the molded body 40 is wedged into the housing sleeve 22. During the wedging in of the molded body 40, the support ring 45 inserted into the ring groove 42 forms a corresponding pressure-sustaining surface for the force used to wedge in the molded body. The thin-wall design of cylinder wall 43 simultaneously ensures that the TEFLON material does not flow too strongly at a temperature stress, for which the TEFLON material of the molded body 40 assumes a doughy state, but retains its position between the support ring 45 and the inside wall of the segment 24. To be sure, the TEFLON material of the molded body 40 expands correspondingly when heated up above 250° C., but returns again to its original state after cooling down, without shrinkage that is worth mentioning. TEFLON material exhibits this behavior with repeated temperature changes. Consequently, the cable bushing is particularly suitable for use in the high-temperature range, e.g., for gas sensors used in exhaust gas systems for internal combustion engines.

The present invention is not limited to the use of gas sensors, but is equally suitable for other seals in the high-temperature range.

What is claimed is:

1. A method for producing a cable bushing which is high-temperature resistant and tightly sealed in a housing for a device which may be a gas sensor and which may be connected to at least one connecting cable having an electrical conductor and cable insulation, the cable bushing having a molded body provided inside an opening of the housing and through which the at least one connecting cable is guided, the molded body having defined therein at least one bushing tube and having an outer cylindrical wall in which is defined a ring groove starting at one frontal side and extending axially inside the molded body, the at least one bushing tube and the ring groove being separated by an inner wall, wherein the inner wall and the outer cylindrical wall of the molded body have respective thicknesses, and the thickness of the outer cylindrical wall is less than the smallest wall thickness of the inner wall, and wherein a support ring is positioned in the ring groove and serves as an outer support for wedging in the molded body into the opening of the housing, the method comprising:

inserting the at least one connection cable into the molded body while outside of the housing;

subjecting the molded body and the inserted at least one connection cable to a heat treatment while outside of the housing so that the cable insulation can at least one of melt on and melt together with the molded body;

inserting a support ring into the ring groove of the molded body;

installing the molded body with the inserted at least one connection cable and support ring into an installed position within the housing; and pressing the molded body while in the installed position into the housing so that the molded body is wedged gas-tight into the housing.

2. The method according to claim 1, wherein the at least one of melting on and melting together during the heat treatment occurs under pressure.

* * * * *